(12) United States Patent
Stark

(10) Patent No.: US 6,403,961 B1
(45) Date of Patent: Jun. 11, 2002

(54) IMAGE GENERATION METHOD

(75) Inventor: Iain Stark, Manotick (CA)

(73) Assignee: IS2 Research Inc., Nepean (CA)

( * ) Notice: Subject to any disclaimer, the term of this patent is extended or adjusted under 35 U.S.C. 154(b) by 0 days.

(21) Appl. No.: 09/404,161

(22) Filed: Sep. 27, 1999

(30) Foreign Application Priority Data

Sep. 25, 1998 (CA) .............................................. 2248424

(51) Int. Cl.$^7$ ................................................ G01T 1/17
(52) U.S. Cl. ............................ 250/363.09; 250/363.07
(58) Field of Search ...................... 250/363.09, 363.07, 250/363.05, 369, 252.1, 370.09, 370.11

(56) References Cited

U.S. PATENT DOCUMENTS

| | | | |
|---|---|---|---|
| 5,185,529 A | * | 2/1993 | Smith et al. ................. 250/369 |
| 5,237,173 A | | 8/1993 | Stark et al. ............... 250/252.1 |
| 5,481,115 A | * | 1/1996 | Hsieh et al. ............ 250/363.04 |
| 5,576,547 A | | 11/1996 | Ferreira et al. ............. 250/369 |

* cited by examiner

*Primary Examiner*—Constantine Hannaher
*Assistant Examiner*—Otilia Gabor

(57) ABSTRACT

An image generation method in a scintillation camera relates to a scintillation camera having a collimator for collimating gamma rays, a scintillation crystal for generating a light scintillation upon receiving a gamma ray, an array of photomultiplier tubes for receiving the generated light scintillation and for generating electrical signals according to amount and position of light received, and a display comprising pixels for displaying an image corresponding to an interpretation of the electrical signals received by the photomultiplier tubes. The method for interpreting the electrical signals received from an array of photomultiplier tubes includes the steps of: receiving electrical signals from the array of photomultiplier tubes; applying a first algorithm to generate a first calculated event position; assigning the first calculated event position to a pixel; applying a second algorithm to generate a second calculated event position; assigning the second calculated event position to a pixel.

6 Claims, 2 Drawing Sheets

IMAGE GENERATION METHOD

FIELD OF INVENTION

The present invention relates to an image generation method in a scintillation camera, and in particular to method for interpreting the electrical signals received from an array of photomultiplier tubes.

BACKGROUND OF THE INVENTION

In the human body, increased metabolic activity is associated with an increase in emitted radiation if the body is appropriately dosed with a radioactive tracer. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. A collimator may vary considerably in weight to match the isotope or study type.

Scintillation cameras are used to take five basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

In generating an image with a nuclear scintillation camera, one of the problems encountered is that there is generally a shortage of detected gamma events.

One reason for the shortage of detected gamma events is that, for health reasons, a patient should be exposed to as little radiation as possible.

The image created by the scintillation camera is essentially a display of detected gamma events. If there are few counts, then there is little data to create the image, and the image may be meaningless from the point of view of human interpretation. It is not that the resolution is poor; it is just that the information is too sparse for a person to discern an image.

To generate an image from detected gamma events, the event information is written into an image or display matrix. Event by event, the data is written into picture elements or pixels. Each element or pixel contains input from zero to a high number of gamma events, proportional to the number of gamma events detected at the location corresponding to that pixel. The more gamma events, the brighter the pixel. A three dimensional graph of the pixels can be generated, showing the X and Y coordinates of the pixel locations in two dimensions, and the number of detected gamma events being indicated by the Z coordinate.

The collimator used in a scintillation camera provides the one to one spacial correlation of the emitted gamma rays at right angles to the crystal. The scintillation crystal used in nuclear scintillation cameras is sensitive. The collimator, however, reduces the efficiency greatly as gamma events occur in all directions, and as the collimator only lets through the gamma events that are substantially perpendicular to the scintillation crystal, most gamma rays are absorbed by the collimator. Collimators generally have efficiencies of minus four or five orders of magnitude; for example, for every 50,000 or so gamma events, only one passes through the collimator and is detected by the crystal.

Only a small amount of radioactive isotope can be administrated to the patient, and most of the gamma events go undetected. With so few counts, an image will not have enough information for form a recognizable picture. As more counts are detected, a pattern becomes discernable; however, details of the pattern cannot be made out; for example, the edge of an object will not be discernable.

Since the patient can only be exposed to a limited amount of radioactivity, one way to generate a better image is to take the picture, i.e. detect emitted gamma events, for a longer period of time. However, there is a limit to the length of time for which a patient can remain essentially motionless. And in some cases, it is impossible for the patient to remain motionless, such as when it is the patient's heart that is being studied. It is common for studies to last for about twenty minutes, during which time the patient must attempt to remain as still as possible as any movement reduces the resolution of the generated image. As the study becomes longer, it becomes more difficult for a patient to remain still, and the resolution of the image tends to deteriorate.

One known method of dealing with the problem of a shortage of information is to apply a smoothing technique to the image data. Basically, smoothing techniques involve moving a certain amount of data from a pixel and moving it to surrounding pixels.

A typical technique or formula is a 121 242 121 smooth. The data associated with a particular pixel is assigned a weighting of 4 relative to its surrounding pixels. The surrounding orthogonal pixels are weighted as 2. The surrounding diagonal pixels are weighted as 1.

With respect to smoothing techniques, a heavy weighting means that the centre pixel is given an high weighting. An example would be a 121 2,20,2 121 smooth. A relatively small amount of data is assigned to surrounding pixels. This is referred to as a light smooth.

With basic smoothing techniques as discussed above, the data is moved without taking into account characteristics of the data as a whole; i.e. the same smoothing technique is applied to each pixel, without taking into account information from other pixels. The result is that the edges of the image become blurred.

A more sophisticated smoothing technique involves weighting the centre pixel by the median value of the nine pixels in the intermediate group. This is called a median smooth. The advantage is that one loses less resolution. The median smoothing technique was developed for looking at eye movements: since an eye generally looks quickly from one place to another.

In the preferred embodiment it is assumed that a tuning device exists, as described in U.S. Pat. No. 5,576,547 and U.S. Pat. No. 5,237,173 but not limited to such devices, and that the tuning is done before the acquisition for the energy information and positional information. The assumption is that before acquisition, tuning is performed on the detector head, which will normalize the responses of all the light detectors. The assumption is that the detector head is digital, but not limited to being digital. (This energy correction method can be used with any detector head on the market which can improve the characteristics of the detector heads.) After or instead of those tuning devices, a new calibration is also performed based on a hole phantom image acquisition.

Another smoothing technique examines the frequency content of the pixels. Smoothing is carried out in frequency space, or Fourier space. The resolution of the system (i.e. the camera that is writing the events into the pixels) can only resolve a certain spacial frequency and not higher. For example, with reference to the collimator, a camera may be able to resolve 4 mm line pairs (i.e. 2 mm of lead, 2 mm gap). This will give a frequency of 4 line pairs per cm. Any higher frequency than cannot be resolved. In between is statistical noise that does not really have a meaning. Thus, the frequency content in the pixels is examined. If the frequency content is above what the system can resolve, then the excess frequencies are filtered out.

Another smoothing technique uses a filter that implements a heavy smooth, and subtracts a light smooth and multiplied by a factor. Such a technique gives an edge enhancement that makes the image look better.

Smoothing techniques allow images to be discerned, but they do not add information. Such smoothing techniques simply spread out the known information so that information can be better interpreted by the human eye. However, in doing so, the spacial resolution of the image is compromised. In other words, the image looks better and patterns can be seen, but, in terms of information theory, information has actually been lost. It must be kept in mind that one will never be able to see something that cannot be seen from the raw or unsmoothed data.

To review, smoothing is generally required to create a recognizable image from insufficient data. However, resolution is lost during the smoothing process.

SUMMARY OF THE INVENTION

An object of the invention is to provide an improved image generation method in a scintillation camera.

A second object of the invention is to provide an improved method for interpreting the electrical signals received from an array of photomultiplier tubes.

According to the invention, there is provided a nuclear scintillation camera having a scintillation crystal for detecting a plurality of nuclear events and for generating a light scintillation corresponding to each detected nuclear event, an array of photodetectors for detecting light scintillations generated by the scintillation crystal, each light scintillation being detected by a plurality of the photodetectors in the array, each of the plurality of photodetectors generating an electrical signal corresponding to the intensity of light detected by that photodetector, a method for generating an image of the distribution and intensity of the nuclear events, the method comprising the steps of: (a) receiving signals from the plurality of photodetectors with respect to each nuclear event; (b) applying a plurality of positioning algorithms to the signals to calculate a plurality of position data, each position data being generated by each respective positioning algorithm; and (c) producing an image using the plurality of position data; whereby, when a small number of nuclear events are detected, a recognizable image can be obtained.

According to the invention, there is further provided a nuclear scintillation camera comprising: (a) a scintillation crystal for detecting a plurality of nuclear events and for generating a light scintillation corresponding to each detected nuclear event; (b) an array of photodetectors for detecting light scintillations generated by the scintillation crystal, each light scintillation being detected by a plurality of the photodetectors in the array, each of the plurality of photodetectors generating an electrical signal corresponding to the intensity of light detected by that photodetector; (c) means for receiving signals from the plurality of photodetectors with respect to each nuclear event; (d) means for applying a plurality of positioning algorithms to the signals to calculate a plurality of position data, each position data being generated by each respective positioning algorithm; and (e) means for producing an image using the plurality of position data; whereby, when a small number of nuclear events are detected, a recognizable image can be obtained.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

DETAILED DESCRIPTION OF THE PREFERRED EMBODIMENT

Figure 1:
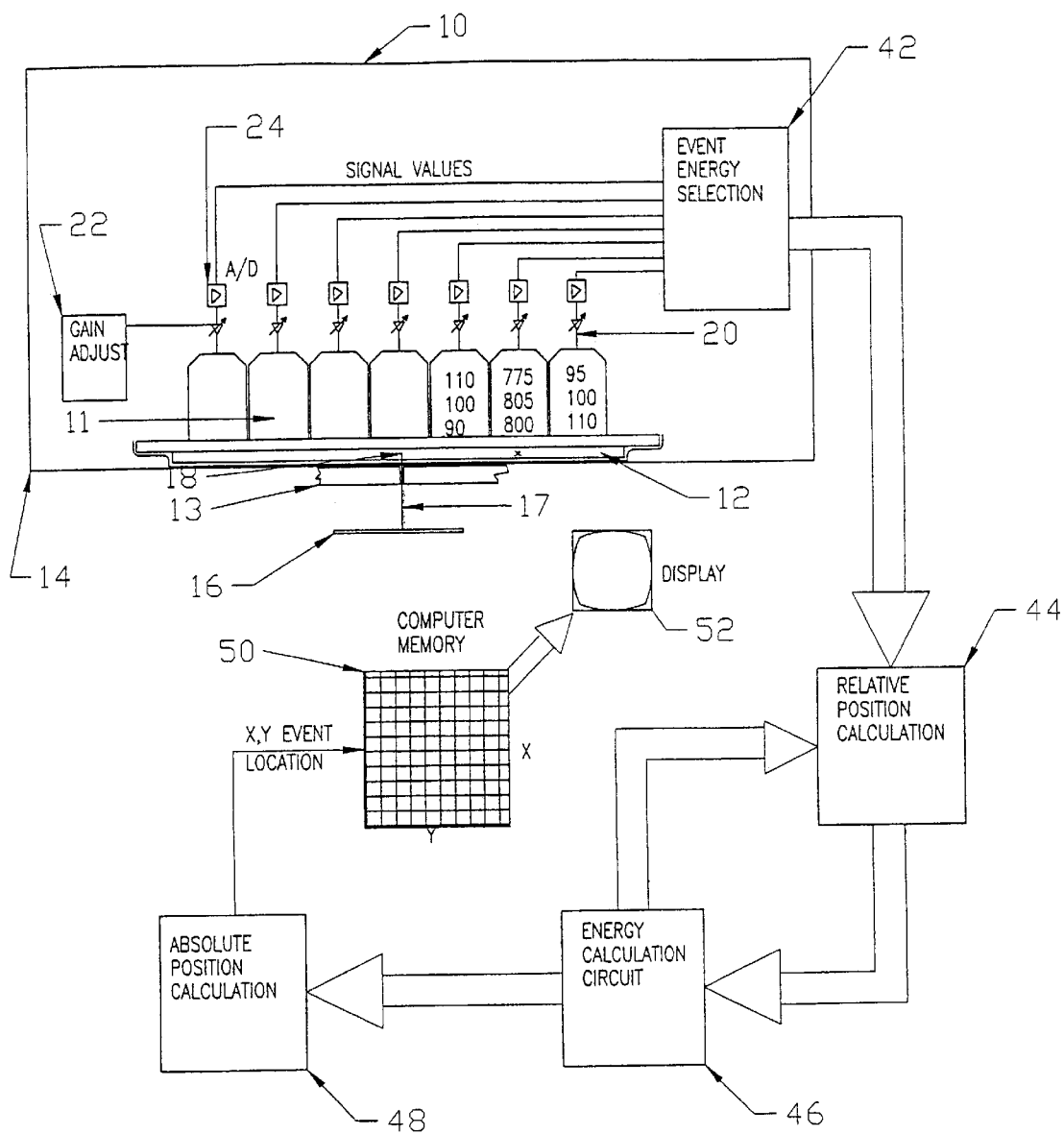
FIG. 1 is a sectional view taken along the line A—A of FIG. 2 showing a scintillation camera head.

FIG. 1 shows the head (10) of a scintillation camera including thirty-seven photomultiplier tubes or photomultipliers (11), a scintillation crystal (12), a collimator (13), and a housing structure (14) by which the components are held together in a unitary manner. The crystal (12) is a disc-shaped, planar scintillation crystal, such as thallium-activated sodium iodide, mounted in the housing (14) by means of suitable shoulders (15). Such crystals are available in different sizes; and a convenient size in wide use at present is 19 inches in diameter.

The collimator (13) is interposed between the crystal (12) and the radiation field (16) and has a plurality of holes, the axes of which are perpendicular to the plane of the crystal, for the purpose of passing only those gamma rays which originate in the radiation field in a region directly beneath the hole. The photomultiplier tubes (11) are conventional in nature and, with a nineteen inch scintillation crystal, it is conventional to use thirty-seven photomultipliers, each of whose diameter is about 3 inches. The photomultipliers are perpendicular to the plane of the crystal, as shown in FIG. 1, and the photocathodes of the photomultipliers are spaced from the upper surface of the crystal (12) in order to optimize the geometrical sensitivity of the photomultipliers. The spacing is chosen so that the geometric sensitivity is constant and has the largest value.

The gamma ray (17) emanating from a point in the radiation field (16) and passing through a hole in the collimator (13) above the point will enter the crystal (12), and, depending on its energy and the thickness of the crystal, will interact therewith at some depth causing light event (18) to occur. Such light event is seen by all photomultipliers. It is the function of the circuitry associated with the head (10) to compute the coordinates of the point in the radiation field causing the light event.

Figure 2A:
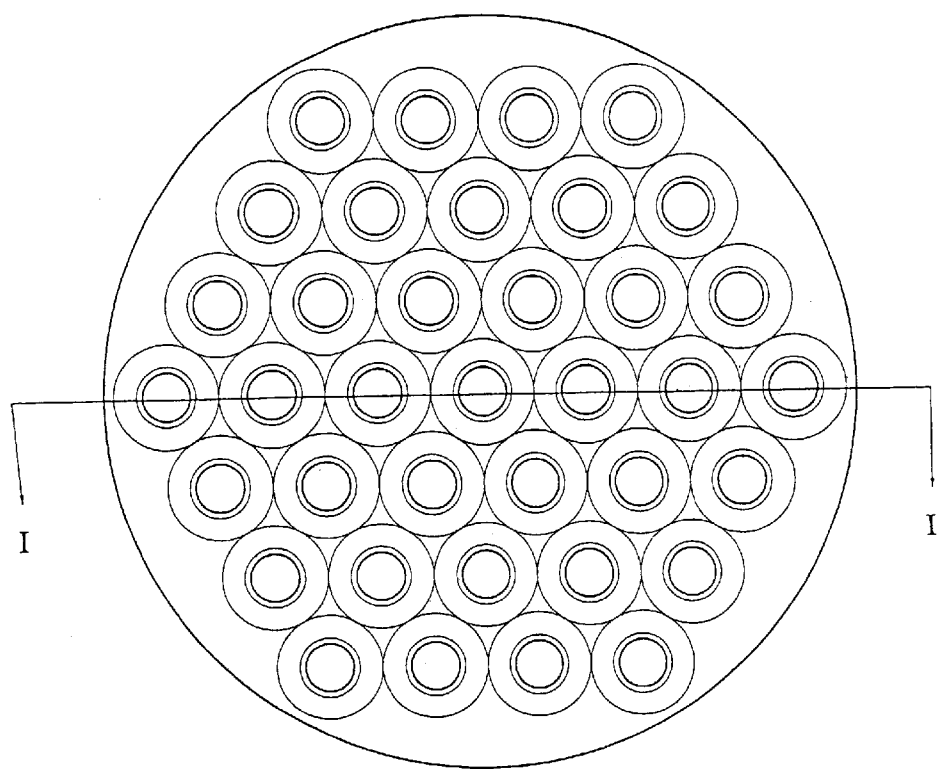
FIG. 2A is a plan view of a scintillation camera head with thirty-seven photomultiplier tubes in a close packed hexagonal array.
Figure 2B:
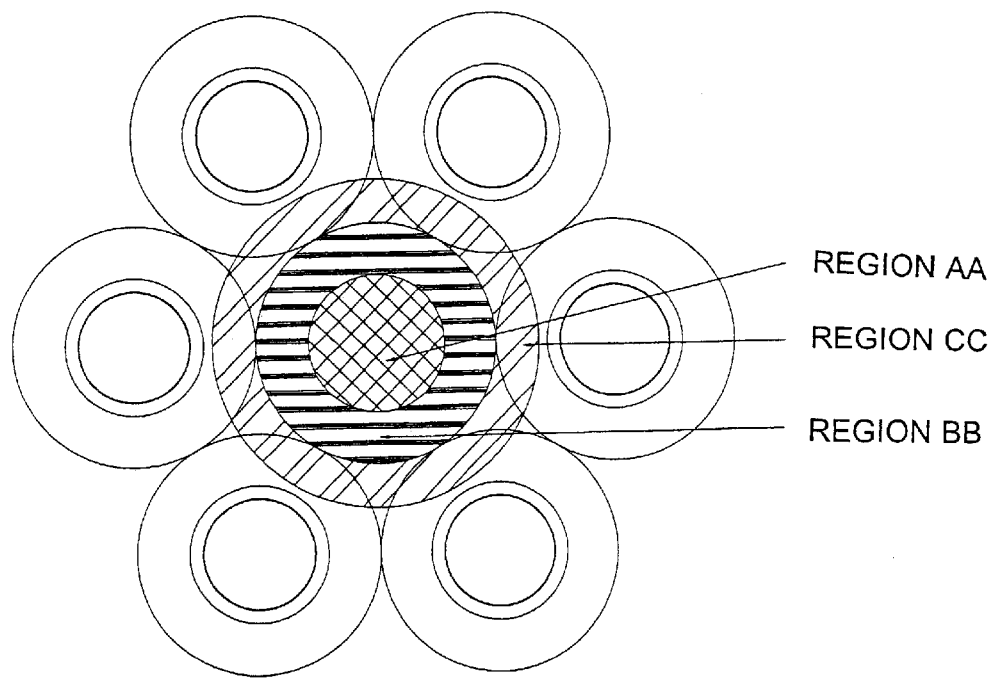
FIG. 2B is an enlarged view of the centre seven photomultiplier tubes with regional algorithmic application.

Before referring to this circuitry, it will be helpful to an understanding of the invention to define some general terms in connection with the array of photomultipliers shown in FIG. 2 since the invention is applicable to other arrays. In general, the motif of any repeating pattern of photomultipliers, regardless of their number, must include at least seven photomultipliers.

FIG. 1 shows the schematic of the system and its functions. The output signals from the photomultiplier tubes are connected to the preamplifier circuits and a variable gain amplifier controller (20) that are provided for each photomultiplier and are controlled by the automatic gain control system (22). The output signals from each preamplifier is connected to the integrating ADC (24) associated with each photomultiplier and the output of the ADC (24) is transferred to the energy selection circuit (42).

Undesirable events are rejected by the energy selection circuit (42) and the desirable events are transferred to the relative position circuit (44). The event position from the energy selection circuit (42) is calculated by the relative position circuit (44) which passes the event relative position information to the energy calculation circuit which loops the information back to the relative position circuit (44) to improve the precision of the calculation. The output of the energy calculation circuit (46) is used by the absolute position calculation circuit (48) with the data from the relative position circuit (44) to produce the absolute XY location of the event to increment the appropriate memory location of the computer memory (50) which is subsequently displayed by the display (52). It is to be understood that the above description is not intended to limit the scope of the invention as defined in the appended claims, as other arrangements are possible.

The position of the gamma event is determined by signals coming from multiple photomultiplier tubes. It is known in the art to calculate the location of the event using an algorithm, and then to apply a smoothing technique. In accordance with the present invention, the location of such events are calculated using more than one algorithm. Thus, by using more than one method to calculate where the event occurred, i.e. use more than one algorithm to calculate the location of the event, then two positions are obtained from one gamma event.

Where the gamma event occurs on the crystal is a single point. At that point a light flash or scintillation occurs. Since the light travels in many directions, the light is generally detected by more than one photomultiplier tube, and a number of photomultiplier tubes generate signals. The photomultiplier tube closest to the scintillation gets the most light and has the strongest outer signal. These photomultiplier tube output signals can be used by more than one algorithm to calculate the position of the event. Note that when, for example, two algorithms are used, the number of events may have to be divided into two groups during certain quantative analyses, depending on their characteristics and relative efficiency of the two algorithms.

If two algorithms are used, both generated images or image data can be written into the display matrix. The image statistics are thus improved because each algorithm uses different aspects and content of the data to derive the position of each event.

Two algorithms are used to calculate the location of each event prior to assigning data to one or more pixels. As long as the signals from the photomultiplier tubes are used by the algorithms in different ways, i.e. as long as the algorithms extract different data from the photomultiplier tube signals, then information is gained.

One of the ways that the processing algorithms should differ is in the way that the algorithms deal with the noise content of the signals from the photomultiplier tubes.

A given algorithm may perform better with respect to signals received from photomultiplier tubes corresponding to different areas of the scintillation crystal. Certain algorithms may perform better within regions of the scintillation crystal or may perform better overall throughout the crystal.

If more then one algorithm is used with a relatively low number of counts, image quality and perceived resolution is improved. This is the situation usually encountered when using scintillation cameras. If more than one algorithm is used with relatively high number of counts, image quality and perceived resolution will generally deteriorate compared with using one algorithm because one of the algorithms will be superior. For a certain number of counts image quality and perceived resolution will be the same for both methods.

In one embodiment of the invention, two or more algorithms can be used until good statistics are obtained. After a time, for the pixels with good information, just the best algorithm may be used; the data obtained by the second best algorithm may either be used or discarded.

The present invention enables better images to be obtained in the same length of time. Similarly, the invention enables similar images to be obtained in less time. While obtaining superior visual quality, less accuracy is lost compared with smoothing techniques.

The resolution of the camera system $R_s$ is given by the formula:

$$R_s = \sqrt{\left(\frac{W_a R_a + W_b R_b}{2}\right)^2 + R_c^2}$$

$R_a$ is the resolution of the first algorithm; $R_b$ is the resolution of the second algorithm; $R_c$ is the resolution of the collimator; $R_s$ is the resolution of the system, $W_a$ and $W_b$ are weighting factors depending on event fractions and correlations of the algorithms.

A gamma ray passing through collimator plate encounters the scintillation crystal which produces light. The crystal does not always produce exactly the same amount of light. The photomultiplier tubes convert light to an electrical signal, which is not always exactly the same. Adjacent photomultiplier tubes may generate the following signals, for example: 90/800/110, 100/805/100, 110/795/95. This sets the limit of the intrinsic resolution, i.e. the resolution of the crystal and photomultiplier tube assembly. The system resolution is the square root of the sum of the squares of the intrinsic resolution and the collimator resolution. The collimator resolution relates to the range of angles at which gamma rays can pass through the collimator, which depends on the apertures in the collimator.

By using a second algorithm, for example, the system resolution may change from 7.74 mm (with a single algorithm) to 7.78 mm (with two algorithms, given an $R_a$=3.3; $R_b$=3.5; $R_c$=7). For this relatively small reduction in resolution twice the number of counts are generated and the image is improved.

Examples of algorithms that can be used may be referred to as the centroid algorithms and the circle algorithm. However, this invention is not algorithm specific, and a number of suitable algorithms can be selected by one skilled in the art.

It should also be noted that the algorithm are to be weighted. One algorithm might be superior in one area, another in a second area, and yet another in a third area. Three algorithms could be differently weighted depending on where the light event occurs relative to the photomultiplier tubes.

With the reference to FIG. 1 the scintillation camera system comprises the digital camera 40, energy rejection circuit 42, relative position calculation 44, energy calculation circuit 46, absolute position calculation circuit 48.

In its preferred embodiment, the energy rejection calculation is digital and independent of the relative position calculation, which means that it can be performed, before, or in parallel with the relative position calculation. If it is performed after relative position calculation then it becomes position dependent. If the energy correction is performed before the relative position calculation, events which are outside the required energy window can be filtered earlier in the process, which improves the efficiency, and hence the speed of the positioning.

In the preferred embodiment it is assumed that a tuning device exists, as descried in commonly assigned application entitled "Photodetector Calibration in a Scintillation Camera Using a Single Light Source" Ser. No. 08/354,546 filed Dec. 14, 1994 or as described in U.S. Pat. No. 5,237,173 but not limited to such devices, and that the tuning is done before the acquisition for the energy information and positional information. The assumption is that before acquisition, tuning is performed on the detector head, which will normalize the responses of all the light detectors. The assumption is that the detector head is digital, but not limited to being digital. (This energy correction method can be used with any detector head on the market, which can improve the characteristics of the detector heads.) After or instead of those tuning devices, a new calibration is also performed based on a hole phantom image acquisition.

Outputs from the digital detector head as seen in FIG. 1, are the following:

1. The label or sequential number associated with the light detector in the detector head T, with the highest response, or in the close neighbourhood of the detector with the highest response. The light detector with the highest response or in close neighbourhood will be called the centre light detector. The assumption is that the absolute coordinates of each light detector is known in the detector head.
2. The response signal of the central light detector of an n-tuple, defining the n-tuple as a group of the light detectors in the neighbourhood of the centre light detector.
3. The responses of all light detectors in the neighbouring n-tuple of the central light detector, defining the n-tuple as a group of the light detectors in the neighbourhood of the centre light detector.

Energy rejection circuit 42, produces a sum signal of said n-tuple of light detector signals including the signal of the central light detector, (E. Relative Position calculation circuit 44, produces x and y values for the particular n-tuple of the light detectors. Output from the position calculation is the associated label or sequential number T of the centre light detector in the n-tuple.

Energy rejection circuit 42 let pass the events with an energy within the peak energy window. For those events, relative position calculation and energy calculation are weakly dependent. Energy calculation may give back an energy evaluation to the relative position calculation, which improves the precision of the position. This loop may be done zero, one or more times.

The energy calculation method consists of three well defined phases: first, acquisition of the energy information; second producing the energy calculation tables; third, applying the energy calculation 46 in real time acquisitions.

Acquisition of energy information: For each of many n-tuples with corresponding central light detector in the preferred embodiment, N by M histograms are recorded which cover the area of calculation of one n-tuple. Each histogram consists of at least 256 bins. Histograms are addressed by the highest n bits of the x position and the highest m bits of the y position. For each event with particular position x and y, particular histogram is chosen depending on position, and the counter of that histogram is increased, depending on the energy. The number of counts in each histogram has to be statistically sufficient. Acquisition is done with the known energy, and without any structured phantoms or collimators.

For producing the energy tables; in the preferred embodiment, histogram should be filtered with a 3D filter for each n-tuple to smooth the response. It is known in the prior art that the response of the light detectors is higher in the centre, and it decreases towards the periphery of the light detector, and that the response is continuous. Responses of the n-tuples are also smooth. For each n-tuple, the maximum response of each of the histograms is computed after filtering. For each histogram the factor should be computed so that the responses of all the light detectors are equal. For each n-tuple, a table of N by M factors is stored in the energy table.

When applying the energy calculation 46 in real time, for each event, and depending on the central light detector of the n-tuple, address or label, and also depending on the first m bits of x coordinate and n bits of y coordinate, a particular address in the table is addressed. The computed energy, which is the sum of all the signals in the n-tuple of light detectors including the central light detector, is multiplied by the factor in the table. This produces the energy calculated value for that event.

In the preferred embodiment, the relative position calculation method consists of four well defined phases. First, acquisition of the position information; second, producing the position calculation tables for each light detector in the n-tuple and third applying the relative position calculation 46 in real time acquisitions. The fourth phase consists of adding the relative position of the n-tuple to the known geometric position of that n-tuple in the scintillation detector to create the absolute position 48. Assumption is that the detector head is capable of providing:

1. Associated label of the light detector in the detector head, with the highest response, or in the close neighbourhood. We will call the light detector with the highest response in one event the centre light detector.
2. Assumption is that the absolute coordinate of each light detector is known in the detector head.
3. Responses of all the light detectors in the neighbouring n-tuple, defining the n-tuple as a group of the light detectors, in the vicinity of the centre light detector.
4. In preferred embodiment n-tuple is consisting of seven or more light detectors.
5. Definition of the event: Event is one incidence of the gamma photon producing the scintillation effect in the crystal of the detector head. Detector head outputs the label T of the centre light detector, and the values of the centre light detector and the intensity values of the light detectors in the neighbouring n-tuple.
6. Positional calculation is the translation of the events from the light detectors output to X, Y and energy values.

In the acquisition of position information; acquisition consists of two parts. First, acquisition with the structured phantom in front of the scintillation camera (similar to Smith phantom), and second, acquisition without phantom, the so-called flood acquisition. Smith phantom is known in the art, and consists of a lead plate with lots of pinholes in a rectangular array. The preferred embodiment uses a hexagonal pattern of holes array, with cycle harmonized to the disposition of the light detectors within the detector head. A mechanism is added to the hexagonal lead plate such that, by manoeuvring one of three levers, the plate may be moved half a distance between two neighbouring holes, so that the resolution along the three axes defining the hexagonal pattern is doubled. Acquisition is done with the radioactive isotope having a known energy. For each of many n-tuples with a corresponding central light detector, in the preferred embodiment, image data is acquired. The images are distorted depending on the geometric arrangement or constellation of the light detectors, the light detector and electronic channel properties, and the method of the position calculation. The position of each pinhole from the phantom is determined. The second acquisition of the flood is needed to determine that the uniformity criterion is satisfied. This means that the number of counts in each area in between the position determined by the image of the pinholes and bounded by the splines which connect all the positions of the pinholes in horizontal and vertical direction. The number of counts in each image has to be statistically sufficient to determine the position of the pinholes, or to check if the uniformity criterion is satisfied.

To apply the relative position calculation 44 in real time; for each event, and depending on the central light detector of the n-tuple, address or label, and also depending on each light detector signal of the n-tuple, a particular address in the table is addressed, which gives a distance from the scintillation to the light detector centre. This is done for each light detector, giving a n-tuple of said distances. Position calculation is performed by solving the linear system of distances. This produces the position calculated value for that event.

Circuit 48 calculates the absolute position correction in real time. For each event, after calculation of the relative addresses and depending on the central light detector of the n-tuple, address or label, the position of the n-tuple is added to the relative position inside the n-tuple to form the absolute address.

In the preferred embodiment, the position calculation method consist of three well defined phases. First, acquisition of the position information, with one radioactive isotope with lower energy (approximately 100 keV) and later with the radioactive isotopes in the medium (250 keV) and high energy ranges (511 keV). Second, producing the expansion correction factors in table form or function with interpolation for the energies between the acquired energies.

In the preferred embodiment, to improve the energy independent position correction method consist of three well defined phases. First, acquisition of the position information; with one radioactive isotope with lower energy (approximately 100 keV), and later with the radioactive isotopes in the medium (250 keV) and high energy ranges (511 keV). Second, producing the expansion correction factors in table form or function with interpolation for the energies between the acquired energies. In circuit 46, the expansion correction factors are applied to the X, Y values calculated in 44, together with the sum of the light detectors values (E given by the energy rejection circuit 42. Although the preferred embodiment illustrates a purely digital camera, it is to be understood that the above described methods can be easily adapted to operate when analog position calculation is used.

The centroid algorithm is used to calculate the incident location of a gamma ray on the crystal of a gamma ray camera detector head. The primary inputs to the algorithm are the energy response signals of an array of photomultiplier tubes (PMTs) that lie on the opposite side of the detector head crystal. PMTs are small (3" diameter) cylindrical devices that detect light rays and output an electrical signal proportional to the intensity of the detected light. The further an event occurred from a PMT the lower its signal.

The first step of the centroid algorithm is to calculate the centroid, or the intensity weighted averaged position of the event. This is calculated by summing the product of the position of each PMT and its energy response to an event, and dividing this sum by the sum of the intensities of each PMT. This can be expressed mathematically as $$c_x = \Sigma pmt_x * pmt_c / \Sigma pmt_c$$

and $$c_y = \Sigma pmt_y * pmt_c / \Sigma pmt_c$$

where ($c_x$, $c_y$) is the centroid calculated position, ($pmt_x$, $pmt_y$) is the position of a PMT, $pmt_c$ is the energy response of this PMT, and the sum is over all the PMTs. This first calculation is very approximate, and weights all events toward the centre of the PMT under which the event happened. As such, it is not clinically useful without further corrections.

The first such correction is that for linearity. A linearity correction table is created by exposing a known configuration of a gamma emitting point sources and calculating the first step centroid for each gamma event. This results in an image of a point sources whose locations have been moved from their actual position due to the known tendency of the centroid method to skew events toward the centre of each PMT. The linearity correction table contains the correlations between the known ("real") position of the gamma emitting source, and the position calculated by the centroid equation. Applying the linearity correction table to the centroid image of the point sources will produce an image of the point sources in their "real" orientation.

Uniformity and energy corrections are subsequently applied to the image, but these are not particular to the centroid algorithm. Linearity correction is also not exclusive to the centroid method, but is absolutely mandatory. Analog cameras use linearity corrections as well, but the pre-linearity corrected images from analog cameras are much closer to the real image than with digital cameras employing the centroid method.

Another algorithm which may be used to calculate the incident location of a gamma ray on the crystal of the gamma camera detector is the "circles" algorithm. As in the centroid algorithm the inputs to the calculation are the measured energy responses of the photomultiplier tubes to the incident gamma ray.

The principle of this algorithm is that the energy response of the photomultiplier tube to a fixed energy incident gamma ray is non-linearly, but monotonically related to the distance of the point of incidence from the centre of that tube via the so called "roll-off" curve, and consequently the energy may be used to determine a circle of possible incidence around each tube. The radius is given as a function of energy r=R(E). Taking the radii and centres of the circles for several such tubes responding to a given gamma event, allows the calculation of a common point of intersection of the circles, localising the point of incidence absolutely.

The incident point (X,Y) of the gamma ray may be calculated after, suitable approximations, using the equation:

$$X = 1/Z \Sigma r_k^2 x_k$$

with a similar form for y. The sum is over the photomultipliers responding to the event, Z is a normalisation constant, $r_k$ is the radius from the centre of the $k^{th}$ PMT, and $x_k$ is the x position of the PMT.

As for the centroid algorithm, the resulting point is approximate and requires corrections for non-linearities of the system.

Numerous modifications, variations and adaptations may be made to the particular embodiments of the invention described above without departing from the scope of the invention, which is defined in the claims.

I claim:

1. In a nuclear scintillation camera having a scintillation crystal for detecting a plurality of nuclear events and for generating a light scintillation corresponding to each detected nuclear event, an array of photodetectors for detecting light scintillations generated by the scintillation crystal, each light scintillation being detected by a plurality of the photodetectors in the array, each of the plurality of photodetectors generating an electrical signal corresponding to the intensity of light detected by that photodetector, a method for generating an image of the distribution and intensity of the nuclear events, the method comprising the steps of:
   a) receiving signals from the plurality of photodetectors with respect to each nuclear event;
   b) applying a plurality of positioning algorithms to the signals to calculate a plurality of position data, each position data being generated by each respective positioning algorithm; and
   c) producing an image using the plurality of position data; whereby, when a small number of nuclear events are detected, a recognizable image can be obtained.

2. A method as defined in claim 1, further comprising the steps of:
   d) weighing the plurality of position data to generate a plurality of weighted position data; and
   e) producing an image using the plurality of weighted position data.

3. A method as defined in claim 2, wherein the step "e" comprises the step of: weighting the plurality of position data in accordance with predefined weighting functions.

4. A method as defined in claim 3, wherein the predefined weighing function is determined depending on the location of the nuclear event.

5. A method as defined in claim 2, wherein the step "d" comprises the step of:
   g) repeating the steps a) and b) to generate statistical information on the performance of each of the plurality of positioning algorithms;
   h) weighing the plurality of position data in accordance with a function of the statistical information on performance.

6. A nuclear scintillation camera comprising:
   a) a scintillation crystal for detecting a plurality of nuclear events and for generating a light scintillation corresponding to each detected nuclear event;
   b) an array of photodetectors for detecting light scintillations generated by the scintillation crystal, each light scintillation being detected by a plurality of the photodetectors in the array, each of the plurality of photodetectors generating an electrical signal corresponding to the intensity of light detected by that photodetector;
   c) means for receiving signals from the plurality of photodetectors with respect to each nuclear event;
   d) means for applying a plurality of positioning algorithms to the signals to calculate a plurality of position data, each position data being generated by each respective positioning algorithms; and
   e) means for producing an image using the plurality of position data; whereby, when a small number of nuclear events are detected, a recognizable image can be obtained.

* * * * *